(12) United States Patent
Mathews et al.

(10) Patent No.: US 6,500,185 B1
(45) Date of Patent: Dec. 31, 2002

(54) SNARE DEVICE

(75) Inventors: Eric D. Mathews, Needham; Paul J. Dobson, Hanover, both of MA (US)

(73) Assignee: Primus Medical, Inc., Hanover, MA (US)

( * ) Notice: Subject to any disclaimer, the term of this patent is extended or adjusted under 35 U.S.C. 154(b) by 0 days.

(21) Appl. No.: 09/676,849

(22) Filed: Sep. 29, 2000

(51) Int. Cl.[7] .............................................. A41B 17/22
(52) U.S. Cl. ....................................... 606/159; 606/127
(58) Field of Search ........................... 606/103, 1, 106, 606/113, 159, 228; 600/585

(56) References Cited

U.S. PATENT DOCUMENTS

| | | | |
|---|---|---|---|
| 2,756,752 A | 7/1956 | Scherlis ....................... 128/303 |
| 3,119,392 A | 1/1964 | Ludwig Zeiss ............. 128/328 |
| 4,706,671 A | 11/1987 | Weinrib ....................... 128/348 |
| 4,745,919 A | 5/1988 | Bundy et al. ................ 128/305 |
| 5,011,488 A | 4/1991 | Ginsburg .................... 606/159 |
| 5,135,531 A | 8/1992 | Shiber ......................... 606/159 |
| 5,143,085 A | 9/1992 | Wilson ........................ 128/772 |
| 5,192,286 A | 3/1993 | Phan et al. .................. 606/127 |
| 5,192,290 A | 3/1993 | Hilal ........................... 606/159 |
| 5,211,183 A | 5/1993 | Wilson ........................ 128/772 |
| 5,217,474 A | 6/1993 | Zacca et al. ................. 606/159 |
| 5,330,482 A | 7/1994 | Gibbs et al. ................. 606/113 |
| 5,441,516 A | 8/1995 | Wang et al. ................. 606/198 |
| 5,527,326 A | 6/1996 | Hermann et al. ........... 606/159 |
| 5,551,443 A | 9/1996 | Sepetka et al. ............. 128/772 |
| 5,554,114 A | 9/1996 | Wallace et al. ............. 604/53 |
| 5,766,192 A | 6/1998 | Zacca .......................... 606/159 |
| 5,840,046 A | 11/1998 | Deem .......................... 600/585 |
| 5,861,024 A | 1/1999 | Rashidi ....................... 607/122 |
| 5,865,767 A | 2/1999 | Frechette et al. ........... 600/585 |
| 5,865,768 A | 2/1999 | Orr .............................. 600/585 |
| 5,876,356 A | 3/1999 | Viera et al. ................. 600/585 |
| 5,895,398 A | 4/1999 | Wensel et al. .............. 606/159 |
| 5,904,657 A | 5/1999 | Unsworth et al. .......... 600/585 |
| 5,916,166 A | 6/1999 | Reiss et al. ................. 600/434 |
| 5,954,737 A | 9/1999 | Lee ............................. 606/159 |
| 5,972,019 A | 10/1999 | Engelson et al. ........... 606/200 |
| 5,984,878 A | 11/1999 | Engelson .................... 600/585 |
| 6,033,423 A | 3/2000 | Ken et al. ................... 606/200 |
| 6,066,158 A | 5/2000 | Engelson et al. ........... 606/200 |
| 6,068,623 A | 5/2000 | Zadno-Azizi et al. ...... 604/530 |

FOREIGN PATENT DOCUMENTS

| EP | 0 418 381 A1 | 3/1991 | ........... A61L/29/00 |
|---|---|---|---|
| WO | 98 25656 A | 6/1998 | |

OTHER PUBLICATIONS

International Search Report issued Mar. 4, 2002 by EPO.

*Primary Examiner*—Gloria M. Hale
*Assistant Examiner*—Alissa L Hoey
(74) *Attorney, Agent, or Firm*—Fish & Richardson P.C.

(57) ABSTRACT

An instrument for removal of an object, e.g., a blood clot lodged in a blood vessel, has a longitudinally extending support that defines an axis. The support has a flexible distal section and a rigid proximal section. The flexible distal section has a compressed state, in which it defines a first path relative to the axis. A core-wire extending along the axis has a relaxed state in which it defines a second path relative to the axis. An anchor disposed on the flexible distal section and attached to the core-wire causes the flexible distal section to follow the same path. An actuator engaged to a proximal end of the core-wire enables a surgeon to selectively apply a tensile force thereto. This tensile force causes the core-wire and the flexible distal section to transition together between the first path and the second path.

31 Claims, 11 Drawing Sheets

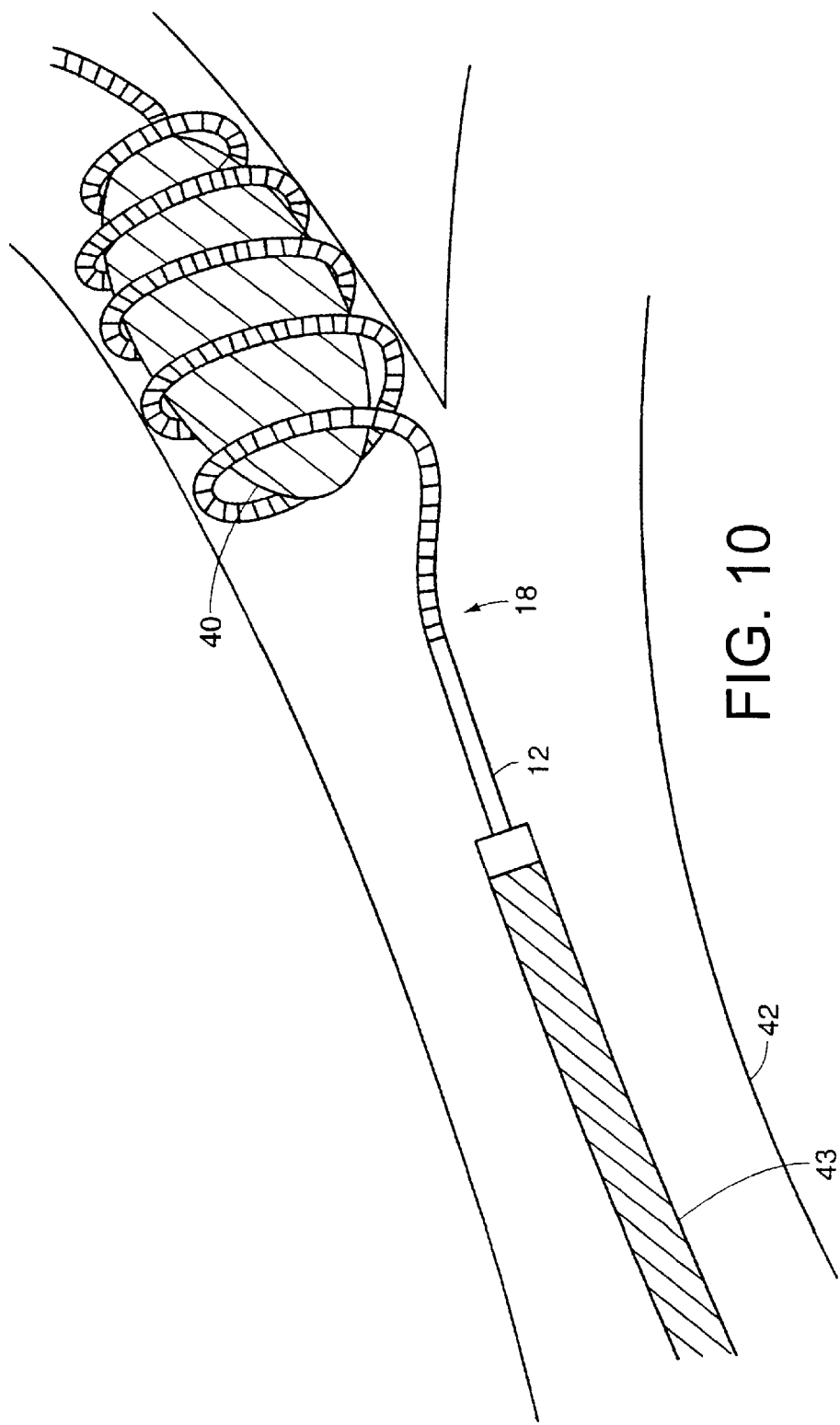

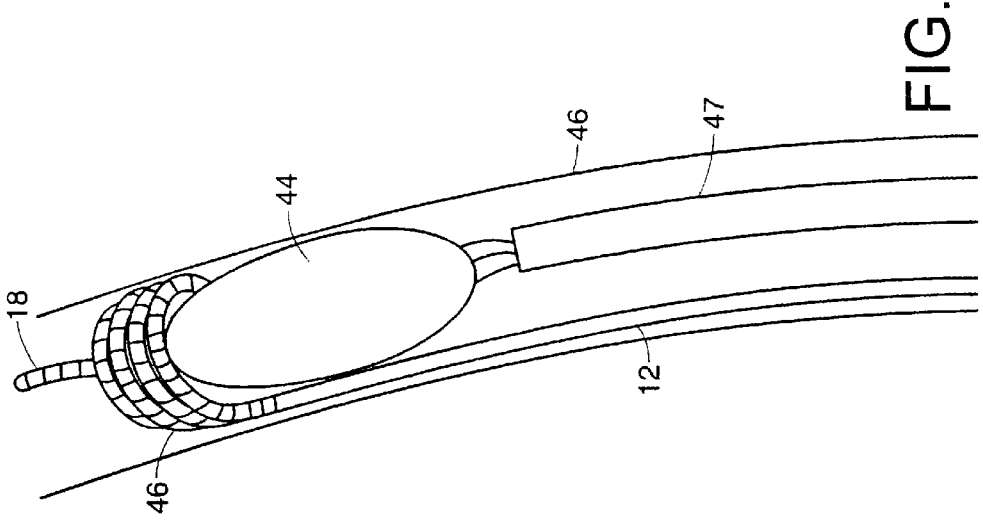
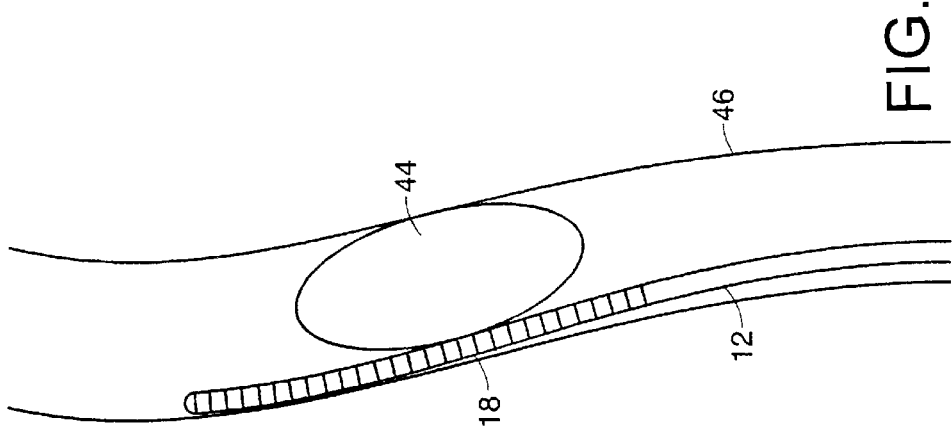

SNARE DEVICE

TECHNICAL FIELD

This invention relates to snare devices, and more particularly to endovascular snaring instruments.

BACKGROUND OF THE INVENTION

A clot in a patient's blood vessel poses grave risks for those portions of a patient's anatomy that are downstream from the clot. Because a clot can inhibit blood flow, cells that rely for their nourishment on blood passing through the obstructed vessel can die. If those cells are particularly essential to life, such as cells associated with the brain or the heart, the patient can also die.

When a blood clot is small relative to the blood vessel, or where the clot is obstructing a relatively minor blood vessel, the patient is generally in no immediate danger. Nevertheless, there does exist the more insidious danger of the blood clot becoming detached and coming to rest again in another blood vessel in which its obstructive effect is less benign. Additionally, there exists the danger that small blood clots migrating through the circulatory system will coalesce with a stationary clot and thereby cause it to enlarge by accretion. When this occurs, a clot of negligible size can grow into a significant obstruction. This growth can occur rapidly because as the clot grows, it introduces more turbulence into the blood flow. This turbulence tends to break up thrombocytes as they pass through the turbulent zone, thereby causing additional clotting.

Conventional methods of removing a blood clot rely on the introduction of medicaments, such as enzymes, that dissolve blood clots. Because the enzymes, such as streptokinase, are introduced into the bloodstream, their effects are systemic rather than local. In addition, the process of dissolving a clot is a time-consuming one during which the patient continues to be in some danger.

Mechanical methods of removing a blood clot have been generally unsuccessful because of the fragility of the clot. When disturbed by a conventional mechanical device, a clot can easily fragment into smaller clots, each of which then begins migrating through the blood stream before settling at an unpredictable location.

SUMMARY OF THE INVENTION

The invention is based on the recognition that when one pulls on a wire, different sections of the wire can be made to stretch by different amounts. This phenomenon is advantageously applied in a surgical instrument having a distal end that readily transitions from an extended state to a coiled state. In the extended state, the instrument can be slipped into an extremely small space, such as the space between a blood clot and the wall of a vessel, without disturbing the clot. In the coiled state, the instrument can ensnare the clot.

In general, the invention features surgical and other instruments that include a longitudinally-extending support member that defines an axis. The support member includes a flexible distal section and a rigid proximal section. The flexible distal section has an equilibrium compressed state and a non-equilibrium uncompressed state. In its compressed state, the flexible distal section defines a first path relative to the axis.

The instruments further include a core-wire that extends along the axis defined by the support member. The core-wire has a relaxed state and a tensioned state. In its relaxed state, the core wire defines a second path relative to the axis. An actuator coupled to the core-wire enables a user, such as a surgeon, to apply a tensile force that pulls on the core-wire. This tensile force places the core-wire under tension and thereby causes it to transition from its relaxed state, in which the flexible distal section is in its uncompressed state, to its tensioned state, in which the flexible distal section is in its equilibrium compressed state.

The distal section of the support member includes an anchor to which the core-wire is attached. This anchor, which can be at any point along the distal section of the support member, provides a mechanical coupling that enables the flexible distal section of the support member to follow one of the first path, as defined by the flexible distal section in its compressed state, and the second path, as defined by the core-wire in its relaxed state.

The core-wire has a distal section having a first yield force and a proximal section having a significantly higher yield force. In one embodiment, the core-wire is made of a super-elastic and shaped-memory metal. In this embodiment, the difference in yield forces is achieved by providing a proximal section with a first cross-sectional area and a distal section with a second cross-sectional area that is smaller than the first cross-sectional area. The distal section of the core-wire is made to have a relaxed state in which it traces a substantially helical or coiled path. The flexible distal section of the support member is made to have a compressed state in which it traces a path substantially parallel to the axis of the support member.

Because the two sections of the core-wire have two different cross-sectional areas, a given force exerted by the user results in more stress in the distal section of the core-wire than it does in the proximal section of the core-wire. This results in the distal section experiencing more strain, and hence greater elongation, than the proximal section. Because the distal section of the core-wire is anchored to the distal section of the support member, the additional length of the core-wire enables the flexible distal section of the support member to revert to its equilibrium compressed state, in which it extends in a direction substantially parallel to the axis of the support member.

Other methods exist of providing a core-wire having sections with different yield strengths. For example, a core-wire can be made of two dissimilar materials having different yield strengths. Or a core-wire can be locally heat-treated to change the yield stress in the heat-treated region.

To ensnare a blood clot, kidney stone, or other object, the surgeon first pulls on the core-wire. This elongates the distal section of the core-wire and hence enables the flexible distal-section of the support member to revert to its compressed state. In this compressed state, the flexible distal-section of the support member defines a line substantially parallel to the axis of the support member. The surgeon then slips the distal-section between the clot and the wall of the blood vessel so that the distal-section of the support member is adjacent to the clot.

Once the distal section of the support member is adjacent to the clot, the surgeon releases the core-wire, thereby restoring the core-wire to its coiled state. This causes the distal section of the support member to also assume a coiled state, and to thereby ensnare the clot alongside it.

The surgical instruments of the invention enable the surgeon to capture a clot and remove it from the blood vessel. In its relaxed state, the flexible distal-section gently cradles the clot within its coils. Since the instrument never penetrates the clot during the removal procedure, the integrity of the clot remains undisturbed. As a result, there is little likelihood that the clot, despite its fragility, will fragment as it is removed. The surgical instruments of the invention thus provide a reliable alternative to the use of systemic medicaments that slowly dissolve a clot.

Instruments embodying the principles of the invention can be used in applications other than the removal of a clot. For example, such instruments can be used to ensnare and remove gall stones. In addition, such instruments can be slipped by a kidney stone and formed into a basket, or strainer, between the kidney stone and the kidney. This basket can then be used to capture and remove kidney stone fragments during lithotripsy. Surgical instruments according to the invention can also be deployed as temporary stents in a blood vessel that has been constricted due to a vasospasm. In this application, the surgeon places the distal end of the support member into its extended state and slips it through the constricted section of the blood vessel. The surgeon then restores the distal end to its coiled state, in which the coils of the distal end dilate the blood vessel and restore blood flow.

Instruments embodying the invention can also be used in non-surgical applications. In particular, such instruments can be used in any application in which it is necessary to ensnare and retrieve an object that is lodged in an inaccessible space. For example, such instruments can be designed to remove clogs from plumbing fixtures or foreign objects from pipes, for example in a food-processing plant, without the need to dismantle the pipes.

In other embodiments, pairs of instruments can be used together to perform tasks that would be difficult to achieve with only a single instrument. For example, to remove a blood clot that is on the other side of a constricted section of a blood vessel, a first instrument can be deployed as a temporary stent while a second instrument retrieves the blood clot after passing through the helix formed by the coils of the first instrument. A first instrument can also be deployed as a basket between a particularly delicate blood clot and the heart, while a second instrument ensnares and removes the blood clot. Any fragments of the blood clot are then captured and removed by the first instrument.

As used herein, the terms "rigid" means sufficiently incompressible so as to retain its form when subjected to tensile and compressive forces but nevertheless able to bend sufficiently to negotiate to negotiate twists and turns in the vasculature or other flow system in which it is to be deployed.

Unless otherwise defined, all technical and scientific terms used herein have the same meaning as commonly understood by one of ordinary skill in the art to which this invention belongs. Although methods and materials similar or equivalent to those described herein can be used in the practice or testing of the present invention, suitable methods and materials are described below. All publications, patent applications, patents, and other references mentioned herein are incorporated by reference in their entirety. In case of conflict, the present specification, including definitions, will control. In addition, the materials, methods, and examples are illustrative only and not intended to be limiting.

The present invention thus offers the advantage of providing safe and rapid removal of obstructions disposed in difficult to access regions. By ensnaring rather than piercing such obstructions, the invention enables the removal of even fragile obstructions without a significant danger of fragmenting those obstructions.

The present invention further provides a temporary stent that can open up a constricted flow channels and restore flow therethrough, even when the constricted flow channel is relatively inaccessible.

Other features and advantages of the invention will be apparent from the following detailed description, and from the claims. The details of one or more embodiments of the invention are set forth in the accompanying drawings and the description below. Other features, objects, and advantages of the invention will be apparent from the description and drawings, and from the claims.

BRIEF DESCRIPTION OF THE DRAWINGS

Like reference symbols in the various drawings indicate like elements.

FIG. 10 is an illustration of the snare in FIG. 9 after having ensnared a clot.

FIGS. 11A and 11B are illustrations of steps in using the snare as a strainer to prevent migration of kidney stone fragments.

DETAILED DESCRIPTION

Surgical instruments described herein use an inhomogeneous core-wire that, when subjected to a pulling force, stretches by different amounts at different locations. At least one portion of the wire has a relaxed state in which it takes the shape of a coil and a tensioned state in which it becomes straight. This portion of the wire is attached to and controls the shape of a flexible portion of the instrument. The tension on the core-wire is controlled by a surgeon selectively pulling and releasing the wire.

Figure 1:
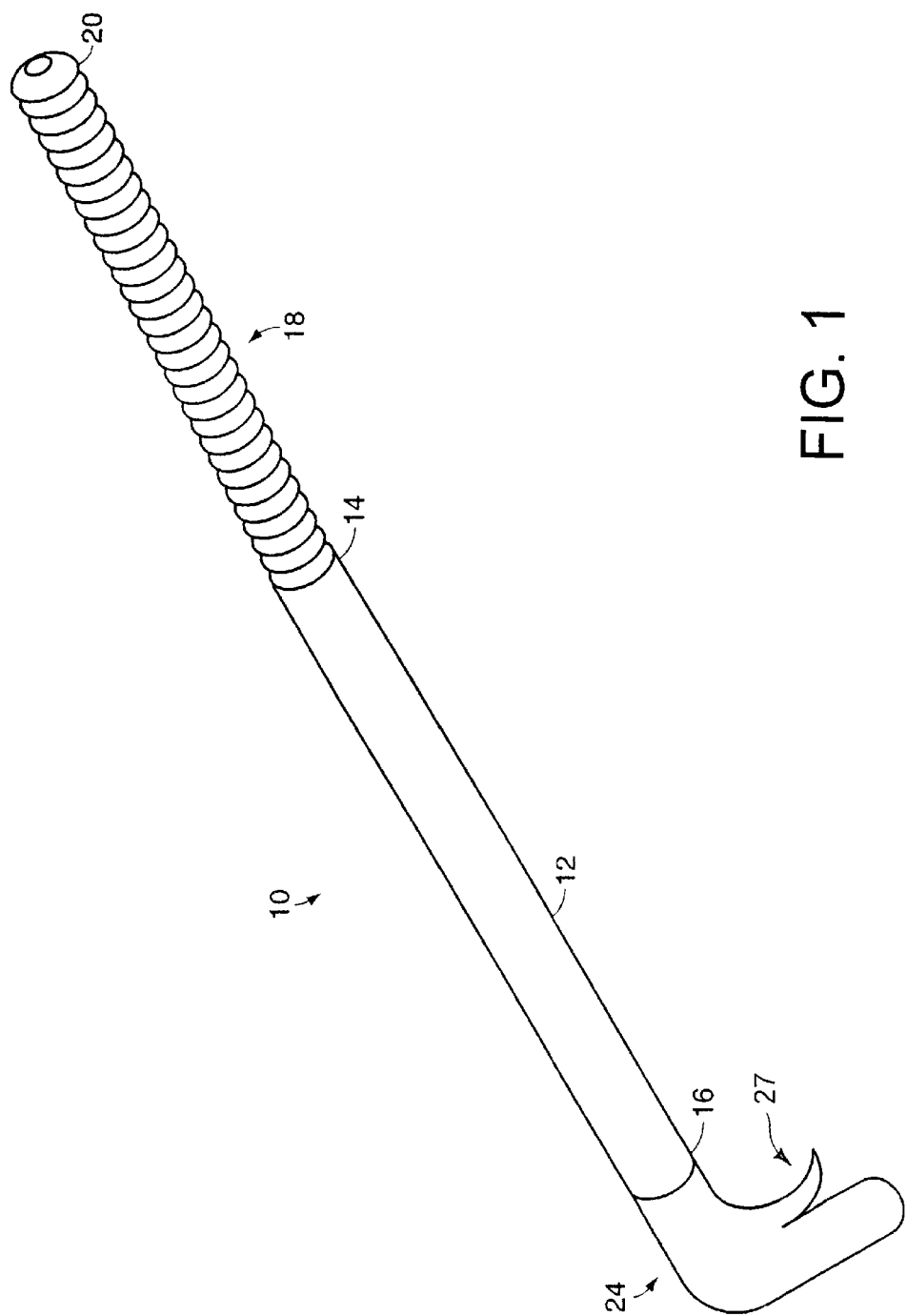
FIG. 1 is an illustration of a snare according to the invention in its extended state.

Referring to FIG. 1, a surgical instrument 10 incorporating the principles of the invention includes a cannula 12 extending along an axis between a distal end 14 and a proximal end 16. A flexible coil section 18 is mounted at the distal end of the cannula 12. The coil section 18 is capped at its distal end by an end-cap 20. Attached to the proximal end 16 of the cannula 12 is an actuator 24 operable by a surgeon to switch the coil section 18 between an extended state, shown in FIG. 1, and a coiled state, shown in FIG. 2.

The cannula 12 in the illustrated embodiment is tubular. However, this is not a requirement. The function of the cannula 12 is to support the coil section 18 when the surgeon applies a force sufficient to toggle the coil section 18 into its extended state. The cannula 12 can be a metal, such as any of the various alloys sold under the trade name NITINOL™, stainless steels, or MP35N®. The cannula 12 can also be made from a polymer, constructed from polyimide, any of the various nylons and polytetrafluoroethylenes such as those sold under the trade name TEFLON®; or it can be a composite tube made from any number of polymers. In addition, the cannula 12 can encapsulate a metallic spring, braid, or similar structure.

Figure 2:
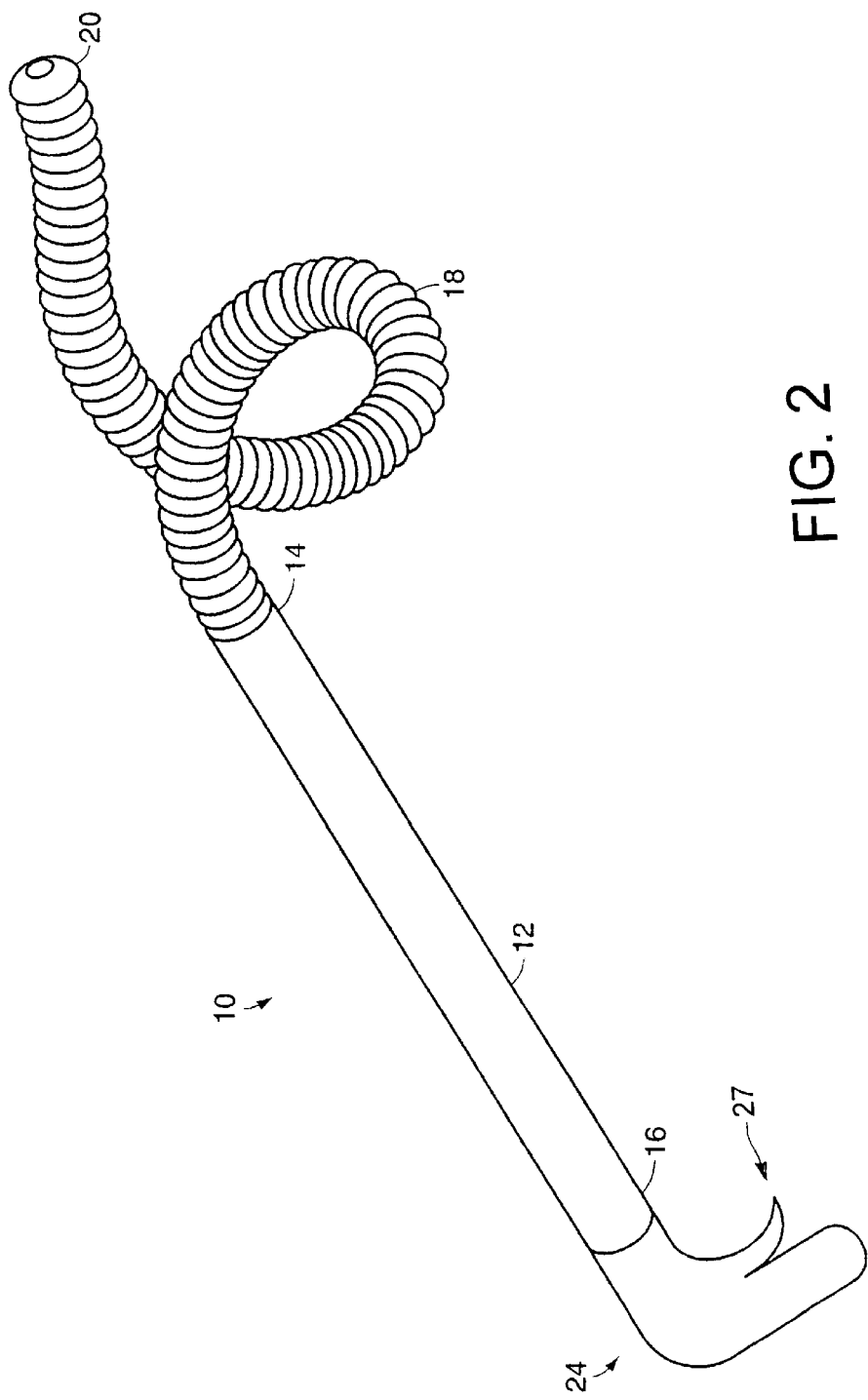
FIG. 2 is an illustration of the snare in FIG. 1 in its coiled state.

As indicated by FIGS. 1 and 2, the coil section 18 is a segmented structure capable of articulation between segments. However, the coil section 18 can also be any flexible section capable of freely making the required transition between the coiled state of FIG. 2 and the extended state of FIG. 1. A preferred coil section 18 has an equilibrium compressed state in which it defines a path corresponding to that shown in FIG. 1. In the illustrated embodiment, the coil section 18 and the cannula 12 are tubular structures that can be coated with a hydrophilic and biocompatible composite material such as PVP. A suitable outer diameter for general intra-vascular use is approximately 0.014 inches.

To enable a surgeon to track the position of the instrument 10 within the body, the coil section 18 can be made of a radio-opaque material such as Pt, W, Ir, Tn, Au, Ag, or an alloy thereof. Alternatively, the coil can be made of coilable polymer, stainless steel, MP35N®, or similar a substance, in which case the coil section 18 is coated with a radio-opaque coating. The coil section 18 may be a close wound coil, with or without preload, or it may be an open wound coil. The coil section 18 may be substituted with baffles, bellows, or any such flexible and compressible member.

Figure 3:
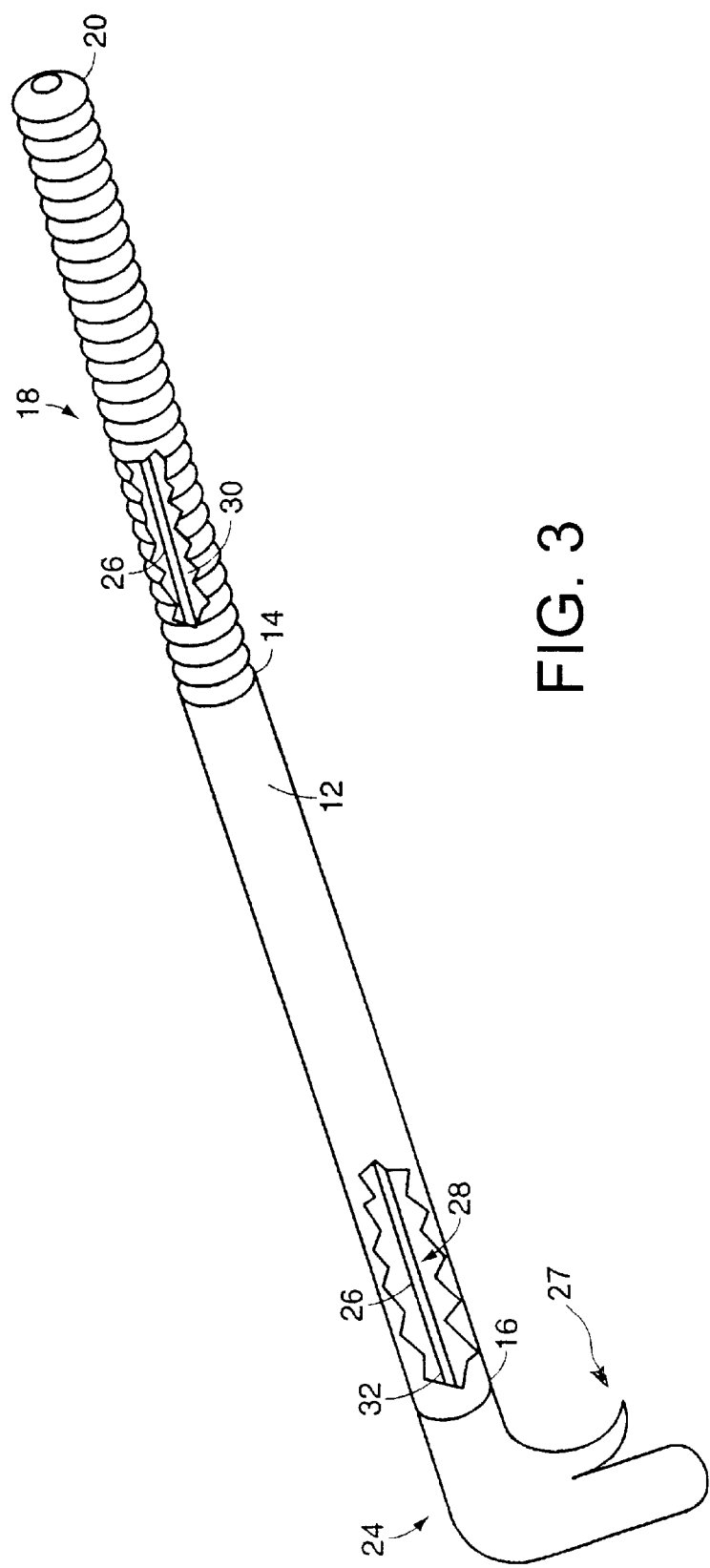
FIG. 3 is a cut-away view of the snare of FIG. 1.
Figure 4:
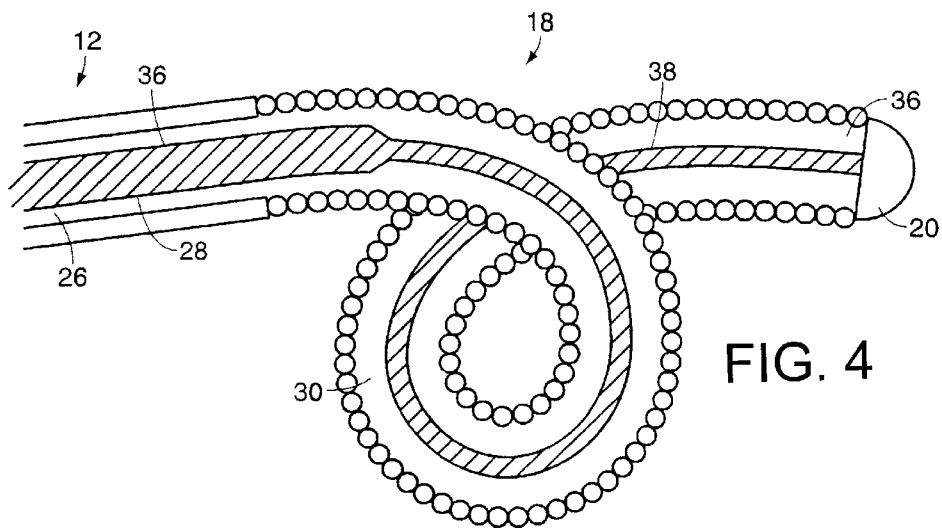
FIG. 4 is a cross-section of the coil section of the snare in FIG. 1.
Figure 5:
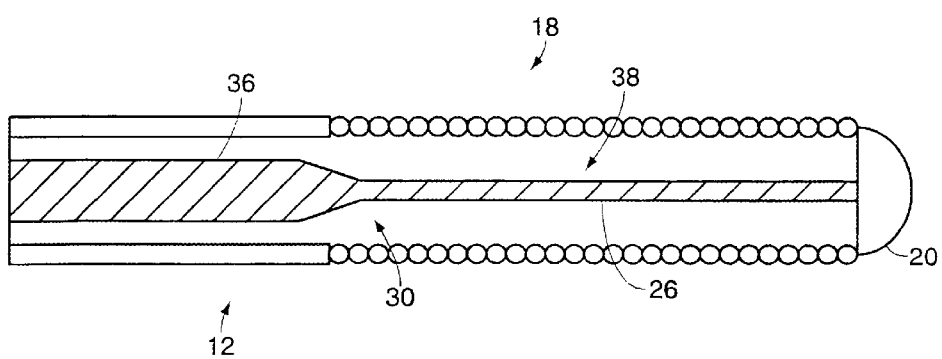
FIG. 5 is a cross-section of the coil section in FIG. 4 with the core-wire in its extended state.

A cut-away view of the surgical instrument 10 shown in FIG. 3, reveals a portion of the structure that enables the surgeon to toggle the coil section 18 between its coiled state and its extended state. As shown in FIG. 3, a core-wire 26 extending from the actuator 24 to the end-cap 20 passes through a cannula lumen 28 and a coil-section lumen 30. The core-wire 26 has a proximal end 32 operably connected to the actuator 24 and a distal end 36 anchored to the coil section 18. In one embodiment, an end-cap 20 functions as an anchoring element on the coil section 18 and the distal end 36 is anchored to the end-cap 20, as shown in FIGS. 4 and 5.

The core-wire 26 is preferably made of a shaped-memory and super-elastic alloy. Such a metal has the property that when deformed and heated past a critical temperature, it "remembers" its deformed shape. When cooled and subjected to further deformation, such a wire springs back to this remembered shape. A suitable super-elastic metal from which the core-wire can be manufactured is a nickel-titanium alloy sold under the trade name NITINOL™. In the case of nickel-titanium alloy, the critical temperature is in the neighborhood of 700 degrees Fahrenheit.

Because the core-wire 26 is anchored to both the end-cap 20 of the coil section 18 and to the actuator 24, and because the coil section 18 is flexible, the core-wire 26 and the coil section 18 follow the same path relative to the axis. When the core-wire 26 is in its coiled state, as shown in FIGS. 2 and 4, the coil section 18 is in an uncompressed state in which it follows the coiled path defined by the core-wire 26. When the core-wire 26 is in its extended state, as shown in FIGS. 1 and 5, the coil section 18 reverts to a compressed state in which it extends along the axis.

Figure 7:
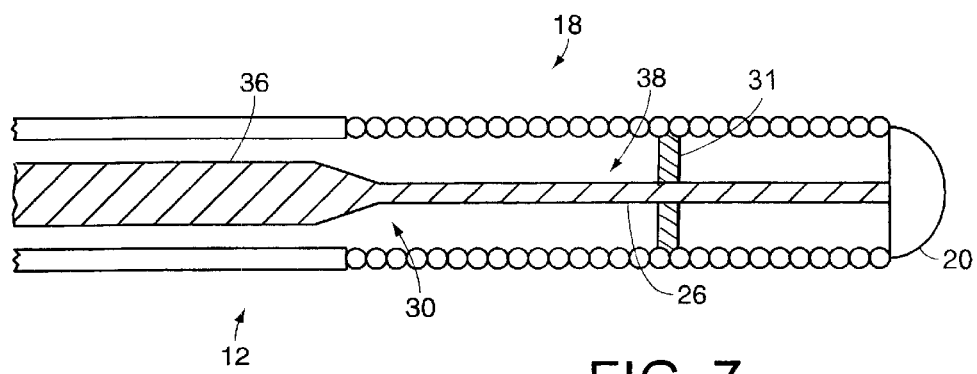
FIG. 7 is a distal section of the coil in which the core-wire is anchored proximally from the distal end to form an atraumatic tip.

The core-wire 26 need not be anchored to the end cap 20. Instead, the core-wire can be anchored to an anchoring element 31 disposed on the coil section 18 at an intermediate point, as shown in FIG. 7. A safety wire 33 extends distally from the anchoring element 31 to the end cap 20 to prevent the coil section 18 from unravelling. This isolates any tensile force applied to the core-wire 26 to points proximal to the intermediate point and results in a coil section 18 having a floppy and atraumatic distal tip, as shown in FIG. 7. An atraumatic tip, such as that shown in FIG. 7, is advantageous because it enables the instrument to be maneuvered in constricted regions without a significant risk of perforating or otherwise damaging surrounding structures.

As shown in FIGS. 4 and 5, the core-wire 26 has two sections: a proximal section 36 that extends through the cannula lumen 28 and attaches to the actuator 24; and a super-elastic - distal section 38 that extends through the coil lumen 30 and attaches to the end-cap 20 of the coil section 18. The proximal section 36 has a yield force that exceeds that of the distal section 38. This enables the distal section 38 to experience more strain for a given tensile force on the core-wire 26 than the proximal section 36.

For a given tensile force, the extent to which a material is stretched depends on its cross-sectional area. This phenomenon is familiar to anyone who has pulled on a piece of taffy and observed that the thin section is far easier to stretch than the thick section. The extent to which the material is stretched is referred to as "strain." The cause of strain is "stress," a quantity which, like pressure, is a force per unit area. Stress can be thought of as pressure acting in the opposite direction. Whereas an applied pressure tends to compress a material, an applied stress tends to stretch a material.

For many materials, no significant strain occurs until a threshold of tensile force is reached. Once that threshold is reached, the material responds readily to additional force. This threshold at which a material begins to respond to an applied tensile force is referred to as the "yield force" of the material.

As noted above, the core-wire 26 transitions from a coiled state to an extended state because the distal section 38 of the core-wire 26 and the proximal portion 36 of the core-wire 26 have different yield forces. This difference in yield forces can be achieved by having a core-wire 26 in which the distal section 38 has a smaller cross-sectional area than the proximal section 36. A differential yield force in the core-wire 26 can also be achieved by having the distal and proximal sections 38, 36 of the core-wire 26 be made of different materials. In such an embodiment, the proximal section 36 would be made of a first material that experiences a negligible amount of strain for a given applied stress. The distal section 38 could then be made of a super-elastic material that stretches readily in response to the same applied stress. The proximal and distal sections 36, 38 of the core-wire 26 could then have the same cross-sectional area but would nevertheless experience different strains when a tensile force is applied to the core-wire 26.

When a surgeon applies a proximally directed tensile force along the core-wire 26, that force causes a stress at each point on the core-wire 26. Because the distal section 38 of the core-wire 26 has a smaller cross-section than the proximal section 36 of the core-wire 26, the stress experienced by those points in the distal section 38 is greater than that experienced by those points in the proximal section 36. Since strain depends on stress, the distal section 38 of the core-wire 26 undergoes more strain than the proximal section 36 of the core-wire 26, and thus becomes significantly longer. This causes the distal section 38 of the core-wire 26 to extend. In this extended state, the core-wire 26 no longer constrains the coil section 18 to follow a coiled path. The coil section 18 is thus free to revert to its equilibrium compressed state in which it extends along the axis, as shown in FIG. 5.

When the surgeon removes the proximally-directed longitudinal force, hereafter referred to as the "tensile force," on the core-wire 26, the distal section 38 of the core-wire 26 reverts to its relaxed state in which it defines a coiled path. Because the core-wire 26 is anchored to the coil section 18, it constrains the coil section 18 to follow the coiled path, as shown in FIG. 4.

The actuator 24 can be a handle with a trigger 27 as shown in FIG. 1. In this embodiment, the trigger is mechanically linked to the core-wire 26 so that when the surgeon pulls on the trigger, a tensile force is applied along the core-wire 26. However, other types of actuators can be used so long as they too apply a tensile force along the core-wire 26. For example, the core-wire 26 can have a handle attached to its proximal end 32, in which case the surgeon pulls on the handle and directly applies a tensile force on the core-wire 26 without any intervening mechanical linkage.

In those embodiments in which the core wire 26 is a wire made of a single material, the diameter of the wire varies along its length. The ratio of the cross-sectional areas of the proximal and distal sections 36, 38 of the core-wire 26 will depend on the material properties of the core-wire 26. The ratio is selected such that a suitable differential strain can be achieved with only a modest exertion of force by the surgeon. The diameters of the two sections of the core-wire 26 are such that the tensile force applied by the surgeon will be insufficient for the core-wire 26 to lose the memory of its remembered shape. In general, this means that the tensile force must be such that the distal section 38 is elongated by less than 8% of its relaxed length, and preferably within 2% to 7% of its relaxed length.

There exist a variety of methods for manufacturing a core-wire 26 having two or more sections that differ in their yield forces. In one method, a continuous wire made of a shaped-memory metal is ground to a smaller diameter to form the distal section 38. The distal section 38 is then heat-set to the desired shape. To achieve actuation of the core-wire 26, there must be a sufficient difference in the yield force of the proximal section 36 and the yield force of the distal section 38. This is achieved by ensuring that the ratio of the diameter of the proximal section 36 to that of the distal section 38 is about 1.35 or greater. For a core-wire 26 having a non-circular cross-section, this is achieved by ensuring that the ratio of the area of the proximal section 36 to that of the distal section 38 is about 1.8 or greater.

The actual transition from one state to another can be viewed as a wave traveling along the core-wire 26. The direction in which this wave travels can be controlled by controlling the taper of the transition between the proximal section 36 and the distal section 38. In the case of a taper as shown in FIGS. 4 and 5, the wave travels from the proximal section 36 to the distal section 38 when the surgeon pulls on the core-wire 26. Conversely, when the surgeon releases the core-wire 26, the wave again travels from the proximal section 36 to the-distal section 38.

Figure 6:
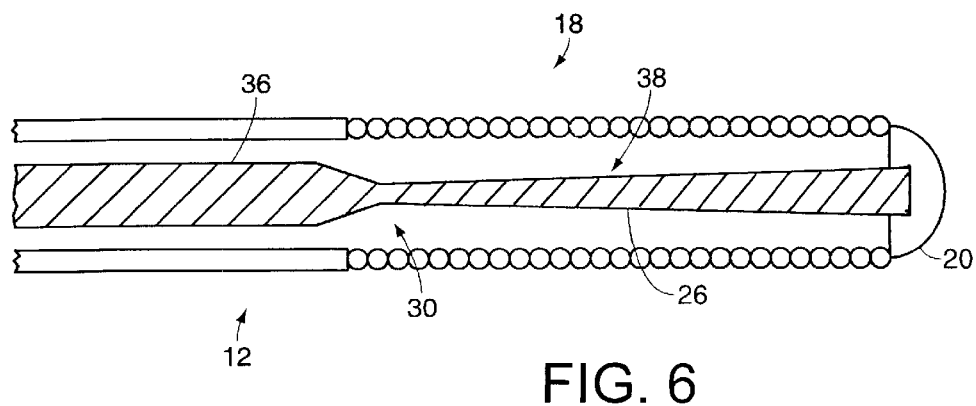
FIG. 6 is a cross-section of a coil section having an alternative transition the proximal and distal sections of the core-wire.

FIG. 6 shows an alternative taper in which the diameter of the core-wire 26 decreases to a minimum as one proceeds distally along the core-wire 26 but then increases to a maximum as the distal section 38 flares to a maximum cross-sectional area at its distal tip,In the case of the alternative taper shown in FIG. 6, the wave travels from the proximal section 36 to the distal section 38 when the surgeon pulls on the core-wire 26. Conversely, when the surgeon releases the core-wire 26, the wave travels from the distal section 38 to the proximal section 36. The ratio of the area of the proximal section 36 to that of the distal section 38 at its tip is about 1.8 or greater In another method of manufacturing the core-wire 26, the yield force in distal section 38 can be reduced by applying heat locally to that section, while masking the heat from the proximal section 36. In some cases, the application of localized heat to form the distal section can eliminate the need to grind the core-wire 26. In other cases, the application of localized heat reduces the ratio of the proximal section diameter to the distal section diameter.

Another method of manufacturing the core-wire is to join a super-elastic distal section 38 to a proximal section 36. This can be achieved by welding or by other means. The proximal section 36 in this case can be made of the same super-elastic alloy as the distal section 38. Alternatively, the proximal section 36 can be made of another metal or alloy such as stainless steel or MP35N®. In either case, what is required is that there be sufficient difference in yield forces between the two sections to enable actuation of the core-wire 26.

Once the distal section 38 is formed, it is then wrapped around a mandrel and heated past the critical temperature of the shaped-memory metal. The core-wire 26 is then cooled, and removed from the mandrel. The resulting core-wire 26 has an equilibrium state in which it is coiled as it was on the mandrel.

To accommodate different size clots, different mandrels can be used. The pitch and number of turns of the coil can be controlled by the manner in which the distal section 38 is wrapped around the mandrel. The number of turns in a coil and the pitch between turns will depend on the specific application. For example, when functioning as a basket for lithotripsy, as described below, the pitch angle is such that the distal section is very tightly coiled to assure capture of most kidney stone fragments. For use as a stent, the number of coils depends on the length of the portion of a blood vessel to be dilated. For general use in removing clots, pitch angles of 15–25 degrees typically provide good results. In practice, a surgeon may have a set of core wires having different sizes and shapes. The surgeon, who presumably has an idea of the size of the clot, selects a core-wire 26 having a distal section 38 that, in its coiled state, encloses a volume only slightly larger than the anticipated volume of the clot.

The shape of the distal section 38 can be customized to treat a number of pathologies or to allow access to hard-to-reach locations in the body. For example, depending on the shape of the mandrel and the manner in which the distal section 38 is wound around the mandrel, the distal section 38 can be a helix with either a closed or open end, a cone, a double-cone shape, or any other shape that would be useful in a particular clinical application. The clinical relevancy of the device is also derived from the forces in the distal section 38. The force required to return to the relaxed state must be optimized for the particular clinical application. This may be accomplished by utilizing any of the core-wire variations described above.

Figure 8:
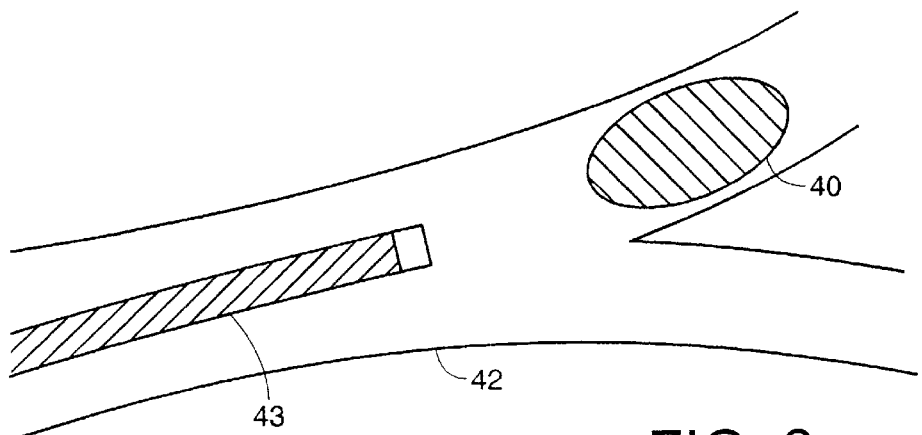
FIG. 8 is an illustration of a catheter for assisting a surgeon in guiding a snare near a blood clot.
Figure 9:
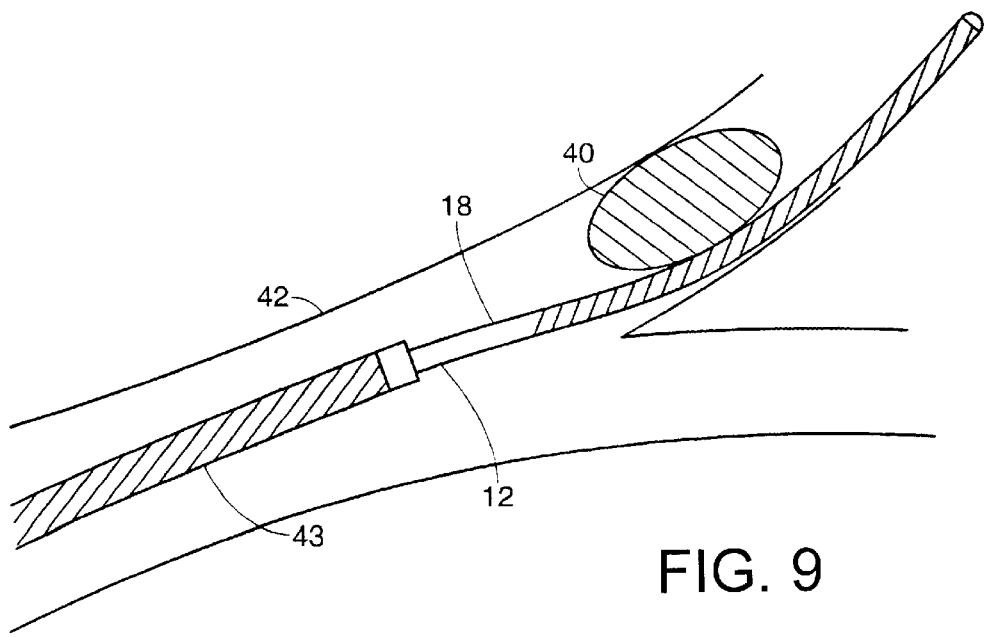
FIG. 9 is an illustration of the snare of the invention extending through the catheter of FIG. 7.

FIGS. 8–10 illustrate the use of the surgical instrument 10 to remove a blood clot 40 from a blood vessel 42. As shown in FIG. 8, the surgeon positions the catheter 43 proximate to a blood clot 40 within a blood vessel 42. The surgeon then passes the surgical instrument 10 through the catheter 43 and maneuvers it toward the blood clot 40.

The surgeon then applies a tensile force to the core-wire 26 and slips the now extended coil section 18 between the blood clot 40 and the wall of the blood vessel 42, as shown in FIG. 9. With the extended coil section 18 adjacent to the clot 40, the surgeon releases the tension to restore the core-wire 26 to its coiled state, as shown in FIG. 10. As the core-wire 26 reverts to its coiled state, it causes the coil section 18 to wrap around the clot 40. With the clot 40 now ensnared by the coil section 18, the surgeon gently removes the cannula 12, and the ensnared clot 40, from the blood vessel 42.

The surgical instrument 10 can be used in applications other than removal of blood clots. For example, FIG. 11A shows the extended coil section being passed between a kidney stone 44 and the wall of a urinary tract 46. In its coiled and uncompressed state, shown in FIG. 11B, the coil section 18 forms a strainer 46 between the kidney stone 44 and the kidney (not shown). This strainer 46 captures any stray kidney stone fragments and prevents them from migrating into the kidney during operation of a lithotripsy device 47.

Figure 12B:
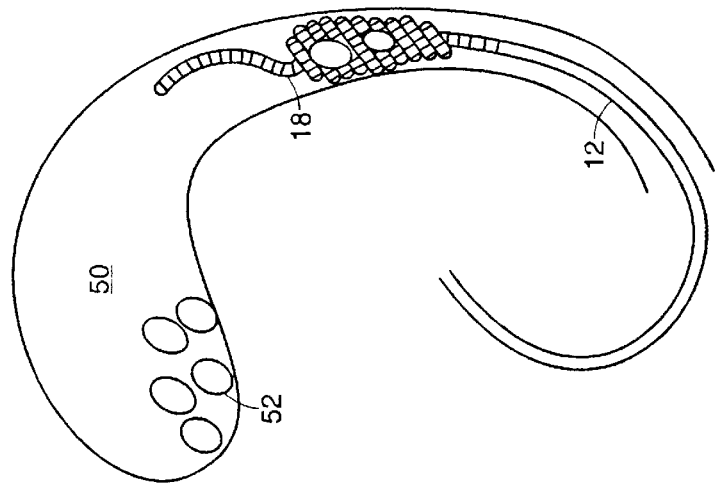
FIGS. 12A and 12B are illustrations of steps in using the snare to capture gall stones.
Figure 12A:
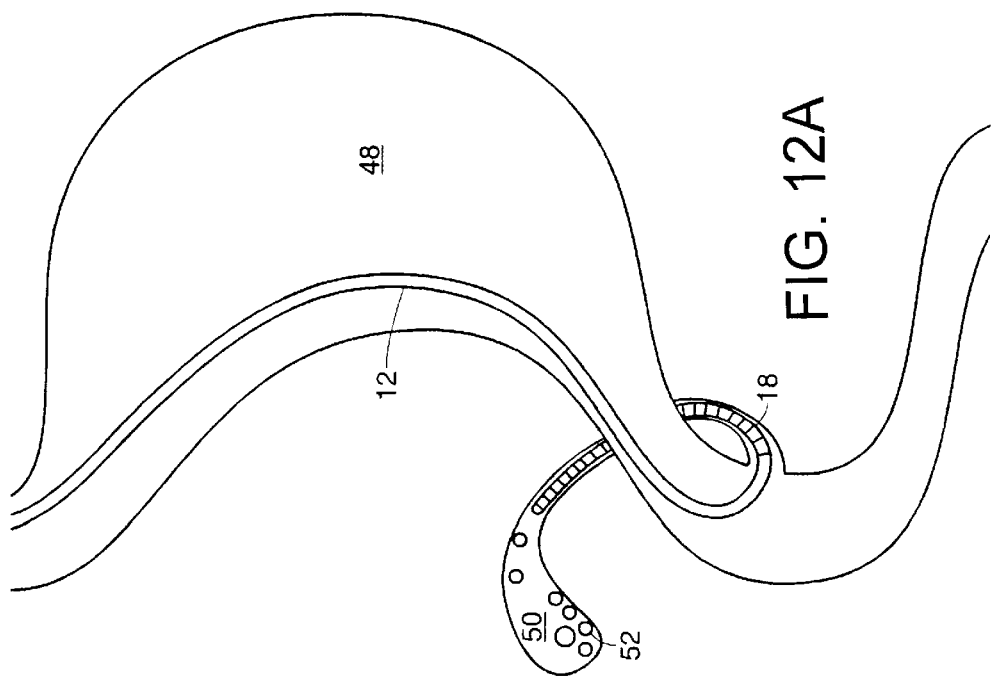

In another application, shown in FIGS. 12A–B, the cannula 12 is passed through the stomach 48 and into the gall bladder 50. In its uncompressed and coiled state, the coil section 18 can be used to ensnare one or more gall stones 52, as shown in FIG. 12B.

Figure 13A:
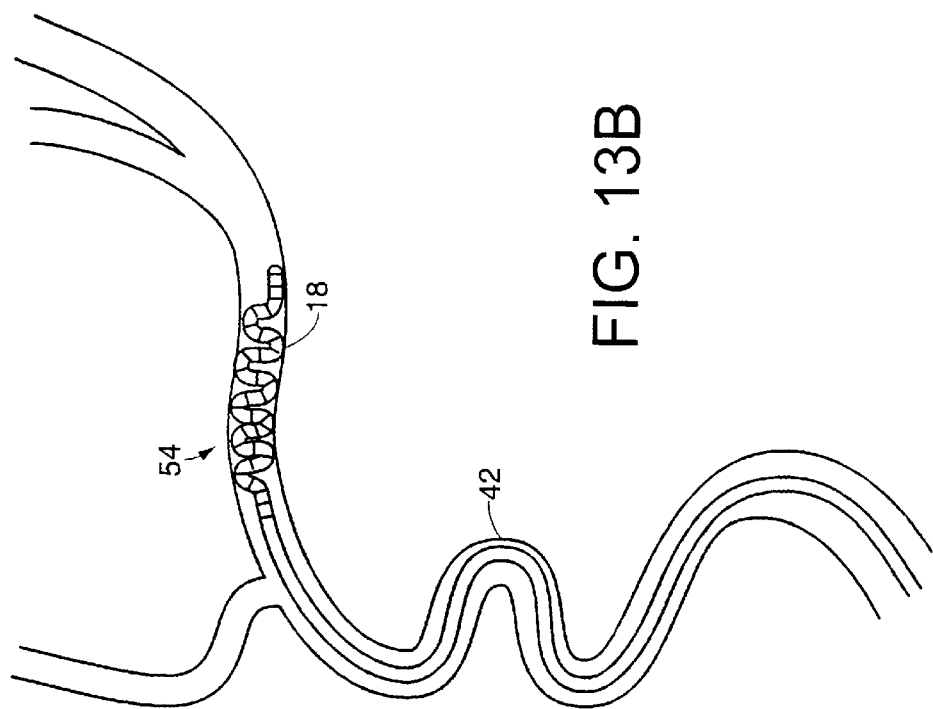
FIGS. 13A and 13B are illustrations of steps in using the snare as a temporary stent.
Figure 13B:
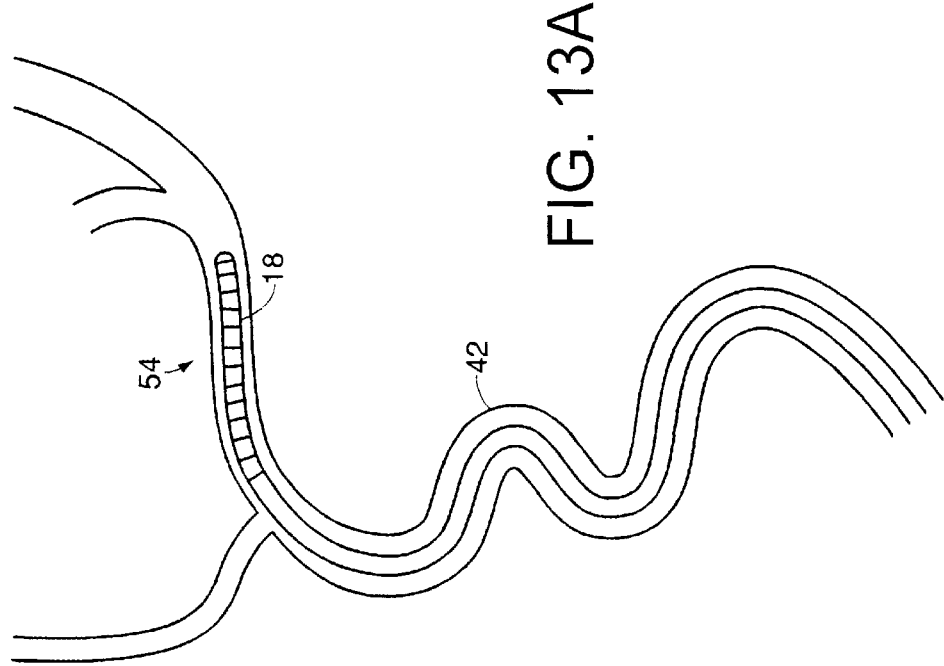

In yet another application, shown in FIGS. 13A–B, the coil-section 18 is slipped through a blood vessel 42 that has experienced a vasospasm. In its extended state, the coil section 18 can pass through the constricted section 54 of the blood vessel, as shown in FIG. 13A. Once the distal end of the coil section 18 has traversed the constricted section 54, the surgeon releases the tensile force on the core-wire 26 and restores the coil section 18-to its coiled state. This results in the formation of a temporary stent 56 that dilates the blood vessel in the region of the vasospasm.

Figure 14:
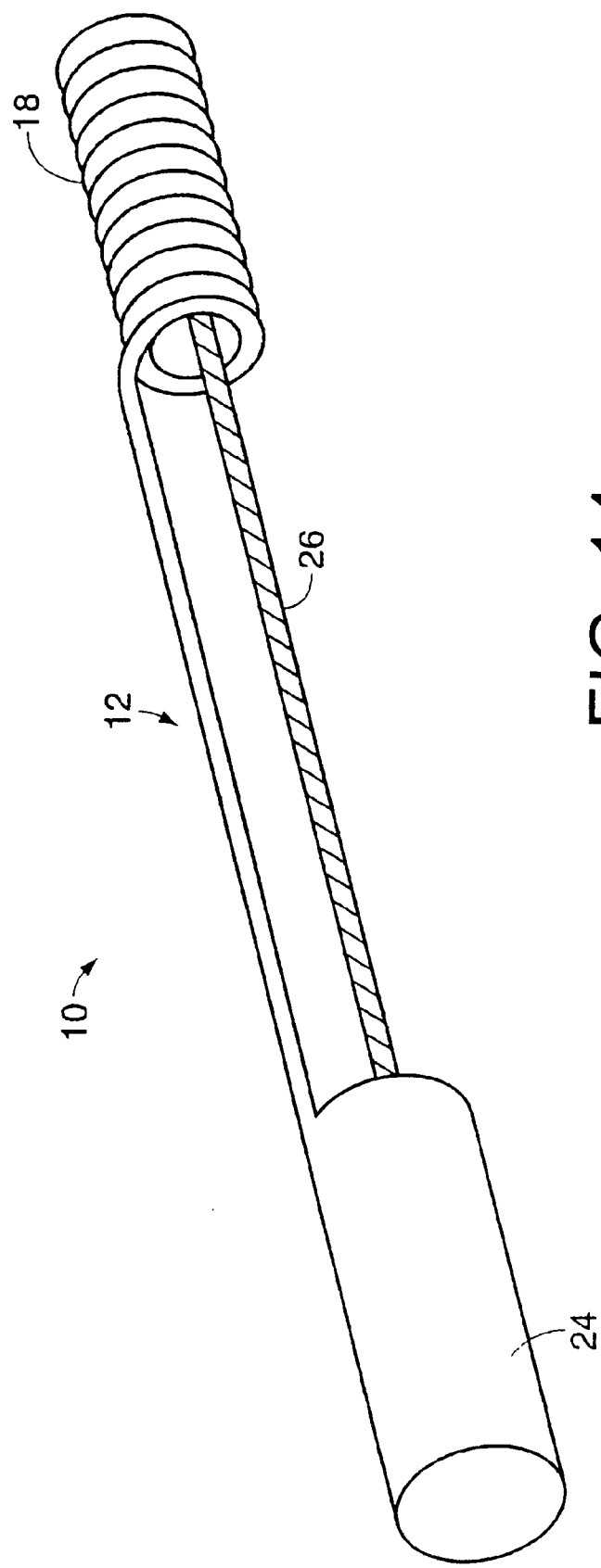
FIG. 14 is an alternative support structure for a snare according to the invention.

The cannula 12 and flexible coil section 18 need not be tubular structures but can instead be open structures as shown in FIG. 14. What is required of the proximal section of the support member shown in FIG. 14 is that it be sufficiently rigid to withstand the force exerted on the core-wire 26.

The cannula 12, the flexible coil section 18, and the core-wire 26 can be coated with a lubricious coating such as PTFE, or any of the various hydrophilic coatings. Other types of coatings can also be used. These include anti-thrombogenic coatings, image-enhancing coatings, or any other procedure-enhancing coating. The friction between the core-wire 26 and the inner wall of the coil section 18 during retraction of the core-wire 26 can also be reduced by providing a lubricious, flexible tube that resides inside the coil section 18.

A surgical instrument 10 constructed as described herein can be used for numerous clinical purposes such as ensnaring and removing clots, emboli, or implants from the cerebral, coronary, and peripheral arteries and veins. The coil's surface area can also be useful for promoting the solidification and adhesion of loose, uncongealed blood clots. Similarly, the device can be used in procedures such as stenting where distal protection is required to capture escaped emboli. The device may have usefulness in penetrating chronic, total occlusions and then expanding the occlusion. One example of this application, already described above, is the use of the surgical instrument 10 to prop open a blood vessel that has collapsed due to spasm or dissection, while allowing blood to flow through dilated blood vessel. The surgical instrument 10 can also be used as a guide-wire to cross lesions and/or deflect and navigate through tortuous vasculatures.

OTHER EMBODIMENTS

A snare constructed along the lines disclosed above has numerous applications other than the clinical applications disclosed thus far. For example, such a snare can be used to retrieve an object that has fallen into a drain, or to remove foreign- objects from pipes, e.g., in a processing plant. A snare according to the invention can also be used to retrieve or remove objects from any type of confined or otherwise inaccessible space.

The instruments can also be designed to capture and retrieve animal specimens from confined spaces. For example, using the instrument, one could easily maneuver through the tunnels of an ant colony to retrieve a particular ant. A larger snare according to the invention can be baited and deployed underground in a mole tunnel to capture moles or other burrowing pests that might consume and destroy valuable horticultural specimens.

It is to be understood that while the invention has been described in conjunction with the detailed description thereof, the foregoing description is intended to illustrate and not limit the scope of the invention, which is defined by the scope of the appended claims. Other aspects, advantages, and modifications are within the scope of the following claims.

What we claim as new, and secured by Letters Patent is:

1. An instrument comprising:
    a longitudinally extending support defining an axis, the support having a rigid proximal section, and a flexible distal section having an uncompressed state and a compressed state, the flexible distal section defining a first path relative to the axis when in the compressed state, wherein a section selected from the group consisting of the rigid proximal section and the flexible distal section includes a tube defining a lumen;
    a core-wire extending along the axis, the core-wire having a relaxed state and a tensioned state, the core-wire defining a second path relative to the axis when in the relaxed state; and
    an actuator engaged to a proximal end of the core-wire for selectively applying a tensile force thereto, the tensile force causing the core-wire to transition from its relaxed state, in which the flexible distal section is in its uncompressed state, to its tensioned state, in which the flexible distal section is in its compressed state.

2. The instrument of claim 1, wherein the core-wire comprises a super-elastic wire.

3. The instrument of claim 2, wherein the super-elastic wire comprises a nickel-titanium alloy.

4. The instrument of claim 1, further comprising an anchoring element for anchoring the core-wire, the anchoring element being disposed at a distal end of the flexible distal section.

5. The instrument of claim 1, further comprising an anchoring element for anchoring the core-wire, the anchoring element being disposed proximal to the distal end of the flexible distal section.

6. An instrument comprising:
    a longitudinally extending support defining an axis, the support having a rigid proximal section, and a flexible distal section having an uncompressed state and a compressed state, the flexible distal section defining a first path relative to the axis when in the compressed state, wherein a section selected from the group consisting of the rigid proximal section and the flexible distal section includes a tube defining a lumen;

a core-wire extending along the axis, the core-wire having a relaxed state and a tensioned state, the core-wire defining a second path relative to the axis when in the relaxed state, said core wire including a first section that experiences a first strain in response to a given tensile force applied thereto; and a second section that experiences a second strain in response to the given tensile force, the second strain being greater than the first strain an actuator engaged to a proximal end of the core-wire for selectively applying a tensile force thereto, the tensile force causing the core-wire to transition from its relaxed state, in which the flexible distal section is in its uncompressed state, to its tensioned state, in which the flexible distal section is in its compressed state.

7. The instrument of claim 6, wherein the core-wire comprises:

a first section having a first cross-sectional area; and a second section having a second cross-sectional area that is greater than the first cross-sectional area.

8. The instrument of claim 7, wherein the ratio of the second cross-sectional area to the first cross-sectional area is at least approximately 1.8.

9. The instrument of claim 6, wherein the core-wire comprises:

a first section made of a first material; and a second section made of a second material, the first and second materials having different stress-strain characteristics.

10. The instrument of claim 9, wherein the first section has a first cross-sectional area; and the second section has a second cross-sectional area that differs from the first cross-sectional area.

11. The instrument of claim 6, wherein the core-wire comprises a super-elastic wire.

12. The instrument of claim 11, wherein the super-elastic wire comprises a nickel-titanium alloy.

13. The instrument of claim 6, further comprising an anchoring element for anchoring the core-wire, the anchoring element being disposed at a distal end of the flexible distal section.

14. An instrument comprising:

a longitudinally extending support defining an axis, the support having a rigid proximal section, and a flexible distal section having an uncompressed state and a compressed state, the flexible distal section defining, when in the compressed state, an extended path that is substantially parallel to the axis;

a core-wire extending along the axis, the core-wire having a relaxed state and a tensioned state, and defining, when in the relaxed state, a coiled path; and an actuator engaged to a proximal end of the core-wire for selectively applying a tensile force thereto, the tensile force causing the core-wire to transition from its relaxed state, in which the flexible distal section is in its uncompressed state, to its tensioned state, in which the flexible distal section is in its compressed state.

15. The instrument of claim 14, wherein the core-wire comprises a super-elastic wire.

16. The instrument of claim 15, wherein the super-elastic wire comprises a nickel-titanium alloy.

17. The instrument of claim 14, further comprising an anchoring element for anchoring the core-wire, the anchoring element being disposed at a distal end of the flexible distal section.

18. The instrument of claim 14, further comprising an anchoring element for anchoring the core-wire, the anchoring element being disposed proximal to the distal end of the flexible distal section.

19. An instrument comprising a flexible tube defining a lumen, the flexible tube having a distal end and a proximal end;

a core-wire extending through the lumen and having a distal end anchored to the flexible tube, the core-wire switching from a relaxed state to a tensioned state in response to a tensile force applied thereto, the core-wire including a proximal portion having a first cross-sectional area and a distal portion having a second cross-sectional area, the ratio of the first cross-sectional area to the second cross-sectional area being at least approximately 1.8; and an actuator engaged to a proximal end of the core-wire for applying a tensile force thereto.

20. An instrument comprising:

a cannula defining a first lumen, the cannula having a proximal end and a distal end;

a flexible tube defining a second lumen, the flexible tube having a distal end and a proximal end mounted on the distal end of the cannula, the second lumen being in communication with the first lumen;

a core-wire extending through the first and second lumens and having a distal end anchored to the flexible tube, the core-wire switching from a relaxed state to a tensioned state in response to a tensile force applied thereto; and an actuator coupled to a proximal end of the core-wire for exerting a tensile force on the core-wire.

21. The instrument of claim 20, wherein the flexible tube is a segmented articulating tube.

22. The instrument of claim 20, wherein the core-wire comprises a super-elastic wire.

23. The instrument of claim 22, wherein the super-elastic wire comprises a nickel-titanium alloy.

24. The instrument of claim 20, wherein the core-wire comprises a proximal portion having a first cross-sectional area and a distal portion having a second cross-sectional area that is less than the first-cross sectional area.

25. The instrument of claim 24, wherein the ratio of the first cross-sectional area to the second cross-sectional area is approximately 1.8.

26. An instrument comprising:

a cannula defining a first lumen, the cannula having a proximal end and a distal end;

a flexible tube defining a second lumen, the flexible tube having a distal end and a proximal end mounted on the distal end of the cannula, the second lumen being in communication with the first lumen;

a super-elastic core-wire extending through the first and second lumens and having a distal end anchored to the distal end of the flexible tube, the core-wire having a first section in which a tensile force on the core-wire results in a first stress and a second section in which a tensile force on the core-wire results in a second stress that differs from the first stress; and an actuator coupled to a proximal end of the core-wire for exerting a tensile force on the core-wire, thereby causing the first section to undergo a first strain and the second section to undergo a second strain different from the first strain.

27. A method for ensnaring an object, the method comprising:

applying a tensile force to a core-wire, thereby placing the core-wire into an extended state;

moving the core-wire, in its extended state, to a position adjacent to the object;

releasing the tensile force, thereby restoring the core-wire to a coiled state and ensnaring the object adjacent to the core-wire.

28. The method of claim 27, further comprising providing a core-wire having a distal section anchored to a support structure and a proximal section in communication with the distal section, the distal section responding to the tensile force by undergoing a first strain and the proximal section responding to the tensile force by undergoing a second strain that is less than the first strain.

29. The method of claim 28, further comprising providing a core-wire made of a super-elastic metal.

30. The method of claim 29, further comprising providing a core-wire having a distal section with a first cross-sectional area and a proximal portion with a second cross-sectional area that is greater than the first cross-sectional area.

31. The instrument of claim 6, further comprising an anchoring element for anchoring the core-wire, the anchoring element being disposed proximal to the distal end of the flexible distal section.

* * * * *